United States Patent [19]

Keimel

[11] Patent Number: 5,591,212

[45] Date of Patent: Jan. 7, 1997

[54] HYBRID BATTERY FOR IMPLANTABLE PULSE GENERATOR

[75] Inventor: John G. Keimel, New Brighton, Minn.

[73] Assignee: Medtronic, Inc., Minneapolis, Minn.

[21] Appl. No.: 505,122

[22] Filed: Jul. 21, 1995

[51] Int. Cl.⁶ .................................................. A61N 1/39
[52] U.S. Cl. ................................................................. 607/5
[58] Field of Search .......................... 607/4, 5, 2; 307/31

[56] References Cited

U.S. PATENT DOCUMENTS

| | | | |
|---|---|---|---|
| 4,599,523 | 7/1986 | Pless | 307/31 |
| 4,868,908 | 9/1989 | Pless | 323/267 |
| 5,131,388 | 7/1992 | Pless et al. | 607/5 |
| 5,265,588 | 11/1993 | Nelson | 607/5 |
| 5,455,999 | 10/1995 | Weiss et al. | 29/623.1 |
| 5,464,453 | 11/1995 | Tong et al. | 29/25.03 |
| 5,522,851 | 6/1996 | Fayram | 607/2 |

OTHER PUBLICATIONS

Sekido et al., "Electric Double Layer Capacitor Gold Capacitor", New Materials and Processes, Matsushita Electric Industrial Co., Ltd., p. 184 (1981).

Morimoto et al., "Characteristics of New Electric Double Layer Capacitor", Proceedings of the 33rd International Power Sources Symposium, The Electrochemical Society, Inc., pp. 618–623 (1988).

Conway, "Transition from Supercapacitor to Battery Behavior in Electrochemical Energy Storage", Proceedings of the 34th International Power Sources Symposium, IEEE, New York, pp. 319–327 (1990).

Bullard, "Operating Principles of the Ultracapacitor", IEEE Transactions on Magneticws, vol. 25, No. 1, pp. 102–106 (Jan. 1989).

Derman, "Electrochemical Caps Diversify", Electronic Engineering Times, Jun. 20, 1994, pp. 58–61.

Primary Examiner—William E. Kamm
Assistant Examiner—Carl H. Layno
Attorney, Agent, or Firm—Reed A. Duthler; Harold R. Patton

[57] ABSTRACT

A power supply arrangement for a battery-powered device includes a high energy density capacitor which is selectively coupled to the device's battery. In one embodiment, the device includes a first circuit which requires a continuous operational power supply voltage to be applied to its power supply input, and further includes a second circuit periodically operates in a peak phase in which it places a high demand upon the device's battery. During normal operation of the device, the first circuit's power supply input and the high energy density capacitor are coupled to the battery so that operational power for the first circuit is provided directly from the battery, and the high energy density capacitor is charged by said battery. During the peak operational phases of the second circuit, the first circuit and high energy density capacitor are decoupled from the battery, such that operational power for the first circuit is provided from the capacitor, while operational power for the second circuit is provided from the battery. During the peak phases, the output voltage of the high-energy density capacitor is monitored, and if it falls below predetermined minimum threshold level, the first circuit's power supply input terminal and the capacitor are temporarily re-coupled to the battery, so that sufficient operational power to the first circuit is ensured.

12 Claims, 2 Drawing Sheets

HYBRID BATTERY FOR IMPLANTABLE PULSE GENERATOR

FIELD OF THE INVENTION

The present invention relates generally to implantable pulse generators, and more particularly, is directed to a hybrid battery for an implantable pulse generator.

BACKGROUND OF THE INVENTION

There are presently two general types of automatic, body-implantable pulse generators used in the treatment of cardiac disorders: pacemakers and defibrillators. These devices are designed to treat abnormal rhythms of the heart known generally as arrhythmias. They are miniature electrical pulse generators typically implanted in either the thorax or the abdominal cavity of the patient and are electrically coupled to the heart by insulated leads with one or more conductors therein for communicating electrical signals between the implanted device and cardiac tissue.

The sinus node is the heart's natural pacemaker. It generates electrical stimuli which are conducted through specialized nerve-like tissue (the atrio-ventricular node) to the lower chambers of the cardiac muscle, affecting muscular contraction of the chambers. During a so-called bradyarrhythmia, conduction of electrical impulses in the heart is partially or completely blocked, causing a delayed contraction or no contraction. An implantable pulse generator functions to maintain the natural rhythm of the heart by sending electrical pulses to the heart in place of a malfunctioning sinus node. The electrical pulses sent by the pulse generator stimulate the heart back into its natural rhythm.

An implantable cardioverter-defibrillator (ICD) functions to restore a patient's heart to a normal rhythm upon detection of cardiac tachyarrhythmia or cardiac fibrillation. In general, the magnitude of cardioverting or defibrillating pulses necessary to terminate an episode of tachyarrhythmia or fibrillation is greater than that of pacing pulses.

Generally speaking, implantable pulse generators can be characterized as being comprised of three primary components: a control circuit, an output circuit, and a power source. An implantable device's control circuit determines, among other things, the rate, synchronization, pulse width, and output voltage of heart stimulating pulses that are generated by the pulse generator. The control circuit may also perform diagnostic functions which are necessary to the safe operation of the generator. An implantable device's output circuit generates electrical stimulating pulses to be applied to the heart via one or more leads in response to signals from the control circuit.

Lithium batteries are generally regarded as acceptable power sources for implantable devices, due in part to their high energy density and low self discharge characteristics relative to other types of batteries. Power must be applied to both the control circuit and output circuit of an implantable device. Typically, the control circuit draws relatively little power from the battery, but must be continuously supplied in order to ensure the ongoing operation of the electronic circuitry typically associated therewith. The output circuit, on the other hand, requires a relatively larger amount of power but draws it mainly during peak demand periods.

In some cases, the power requirements of an implantable device's output circuit are higher than the battery can deliver. Thus, it is common in the prior art to accumulate and store the stimulating pulse energy in an output energy storage device at some point prior to the delivery of a stimulating pulse. (Most often, the output energy storage device comprises a capacitor, although it is contemplated that other types of energy storage devices could serve this purpose. For the sake of simplicity, however, the term "output capacitor" will be used herein to refer to the energy storage device in the output circuit.) When the control circuit indicates to the output circuit that a stimulating pulse is to be delivered, the output circuitry causes the energy stored in the output capacitor to be applied to cardiac tissue via the implanted leads. Prior to delivery of a subsequent stimulating pulse, the output capacitor must be recharged.

One perceived drawback of prior implantable pulse generators is that they often have to be replaced before their battery depletion levels have reached a maximum. When an implantable device's output capacitor is being recharged, there is a drop in battery voltage due to the charging current flowing through the battery impedance. Although this voltage drop may not be significant when the battery is fresh, over time the battery ages, causing its internal impedance increase or its peak output voltage to decrease, such that the voltage supplied to the control circuit may drop below a minimum allowable level. This temporary drop can cause the control circuit to malfunction. The implantable pulse generator must be removed and replaced before any such malfunctions occur, even though the battery may still have sufficient capacity to stimulate the heart. For this reason, most implantable device manufacturers specify battery end-of-life (EOL) criteria which are met prior to complete depletion of the battery.

In the context of cardiac pacemakers, one approach to the problem of battery voltage drop during output capacitor recharging has been to provide a priority switching circuit which provides a minimum voltage to the control circuit while the output capacitor is being recharged. Such an arrangement is disclosed, for example, in U.S. Pat. No. 4,599,523 to Pless et al. entitled "Power Priority System." The device disclosed in Pless a priority switching circuit which utilizes a hold-up capacitor of approximately 10- µF which is connected in parallel with the control circuit and which is charged during the off-peak demand cycles of the charging/output circuit. In a peak demand cycle, the battery is disconnected from the control circuit and connected to the output circuit. During this time, the hold-up capacitor supplies the control circuit with a minimum operating voltage. The switching circuit of this device is designed to default to the control circuit, so that if the drain on the hold-up capacitor is too great during charging of the output capacitor, the battery is temporarily disconnected from the output circuit and reconnected to the control circuit, also recharging the hold-up capacitor. This insures that a minimum voltage is always supplied to the control circuit. This approach is feasible in the context of a cardiac pacemaker, which simply charges a capacitor to a few volts, imposing a high a high current drain on the battery for a period of 10–20 milliseconds, as the hold-up capacitor can be quite small.

In the context of an implantable defibrillator, which may charge an output capacitor bank to over 700 volts, over a period of up to 30 seconds or more, alternative solutions to the problem of voltage drop during charging have been proposed. One such solution is to provide two batteries, one for charging the output capacitor and a separate battery for powering the control circuit. Such was the case, for example, in the Model 7210 ZSX implantable cardioverter, manufactured for clinical investigation by Medtronic, Inc., Minneapolis, Minn. One problem with this approach, is that the relative amounts of energy required in a device for the control and charging/output circuitry will vary from patient to patient. The capacity of the battery to power the control circuit can only be optimized with regard to one patient profile. For all other patients, one battery will deplete before the other battery, leaving wasted energy in the device. Thus, for a given required device longevity, the overall battery capacity needed to power the control circuit and the charging/output circuit separately with two power sources can be greater than the capacity needed to power them together with one power source.

As a practical matter, the battery chemistries used in implantable defibrillators do not provide a single cell voltage levels which will simultaneously allow for acceptable charging times, provide adequate voltage levels during capacitor charging and provide a reasonable device longevity. Thus, commercially marketed implantable defibrillators employ multiple cell batteries to provide sufficiently high voltages. However, this approach still provides less than optimal device longevity, for the reasons discussed above. Further, if possible, a single cell battery would be preferable to a multiple cell battery of the same capacity.

SUMMARY OF THE INVENTION

The present invention is directed to an improved method and apparatus for providing power for body-implantable medical devices such as implantable defibrillators, which have circuitry or other powered apparatus which draw high levels of current for extended periods of time, and which also employ control circuitry which concurrently requires a minimum operating voltage. The present invention is believed to be particularly suitable for implementation in connection with implantable defibrillators and cardioverters, wherein the demands placed upon the power supply by the charging/output circuitry are especially great.

In accordance with one aspect of the present invention, a high value, high energy density capacitor is utilized to supply power to control circuitry in a battery-operated device during peak current demand periods. During off-peak demand periods, the high energy density capacitor is coupled to the battery and is charged to the battery's output voltage. During periods of increased demand on the battery (e.g., during an output capacitor charging period, the control circuitry and capacitor are decoupled from the battery output, and receives its operational power from the high energy density capacitor.

In accordance with another aspect of the invention, if the output voltage from the high energy density capacitor falls below a predetermined level, the control circuitry and capacitor are recoupled to the battery output. In addition, the operation of circuitry which is responsible for the increased battery demand (e.g., the output capacitor charging circuitry) is temporarily interrupted, giving the battery time to recover and the high energy density capacitor to be recharged. Once this occurs, the control circuitry and high energy density capacitor are again decoupled from the battery, and the period of high battery demand is resumed (e.g., the charging period is resumed). The high energy density capacitor is chosen to have a value which will allow it to power the control circuitry for an extended period of time, (at least 1 second, preferably 5–30 seconds or more) preferably sufficient to allow the high current drain function to be completed without interruption, or with a minimum number of interruptions.

DETAILED DESCRIPTION OF A SPECIFIC EMBODIMENT OF THE INVENTION

As noted above, it is believed that the present invention may be particularly well-suited to the power supply needs of implantable cardioverter-defibrillators; accordingly, the invention will be described below in the context of such a device. However, the present invention may also be advantageously practiced in connection with other classes of battery powered implantable devices which intermittently perform operations which impose a high current drain on the battery, including but not limited to implantable long-range telemetry systems, implantable drug pumps, or other devices which include pumps or other electromechanical apparatus.

Figure 1:
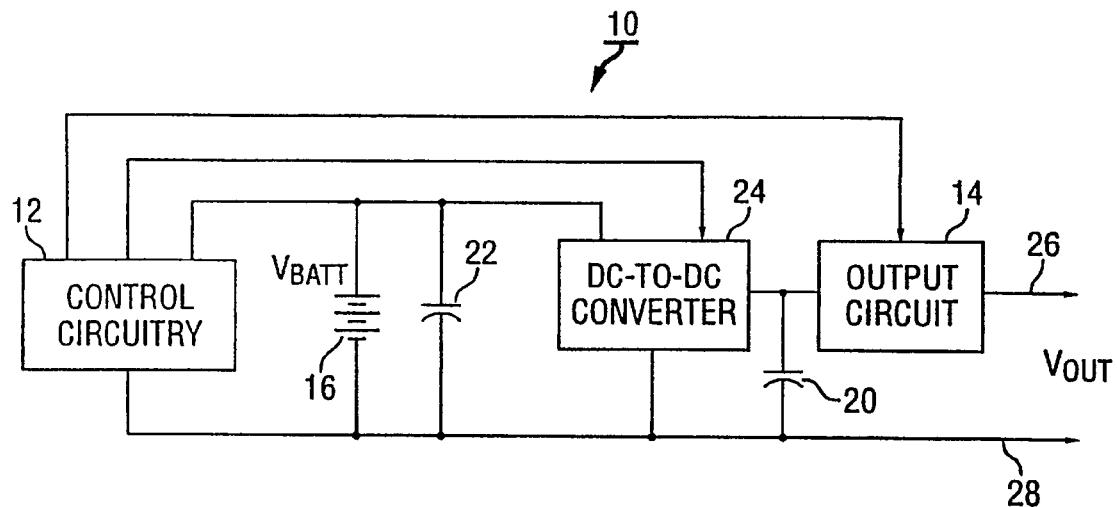
FIG. 1 is block diagram of a prior art battery-powered implantable medical device.

Referring to FIG. 1, there is shown a schematic/block diagram of a conventional (i.e., prior art) implantable defibrillation pulse generator 10 including a control circuit 12, an output circuit 14, and a battery 16. A more detailed disclosure may be found in U.S. Pat. No. 5,265,588, issued to Nelson et al and incorporated herein in its entirety. Pulse generator 10 includes an output capacitor bank 20, (e.g. two 240 microfarad capacitors connected in series) for storage of defibrillation pulse energy to be delivered to the patient in accordance with control signals issued by control circuit 12. A lower value capacitance 22 (e.g. two 33 microfarad capacitors in parallel) is connected parallel to the battery, which powers the primary winding of a flyback transformer within DC to DC converter 24. Capacitance 22 serves as a low impedance source for the flyback transformer and also reduces power supply noise. In accordance with conventional practice, DC-to-DC converter 24 functions to charge output capacitor 20 to an energy level appropriate for cardioversion or defibrillation, which may be up to 750 volts, under control of control circuit 12. With continued reference to FIG. 1, once output capacitor 20 is charged, output circuit 14 is responsible for applying stimulating pulse energy ($V_{out}$) between output terminals 26 and 28 of device 10, which terminals are customarily coupled to the conductors of implantable cardiac leads (not shown).

Figure 2:
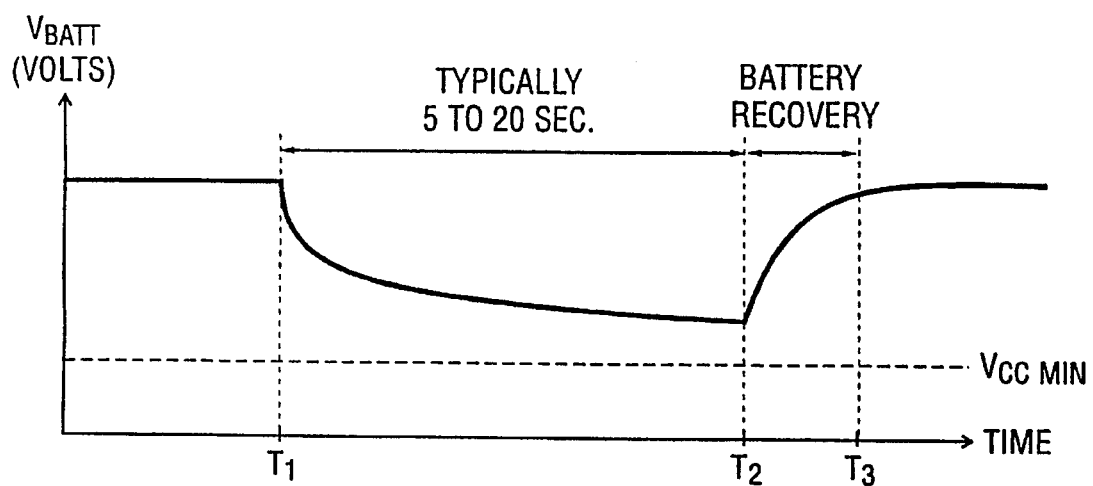
FIG. 2 is a plot of the battery output voltage versus time for the device of FIG. 1.

In FIG. 2, there is shown a plot of battery voltage $V_{BATT}$ versus time during a charging period for device 10 from FIG. 1. At time T1 in FIG. 2, a charging period is initiated wherein DC-to-DC converter 24 begins drawing current from battery 16 to charge output capacitor 20. The charging period lasts until time T2 (typically 5 to 30 seconds for implantable cardioverter/defibrillators), at which point drain on battery 16 ceases and battery 16 begins a recovery phase between times T2 and T3 in which $V_{BATT}$ rises toward its pre-charging-period level. As a result of the drain on battery 16 during the charging period, the battery voltage $V_{BATT}$ drops, as shown in FIG. 2. The maximum power is transferred from the battery (and hence charge cycle time is minimized) when $V_{BATT}$ drops during the charging period to approximately one-half of the battery's open-circuit voltage. Of course, such a 50% drop in $V_{BATT}$ cannot be realized if the battery's open-circuit voltage is less than twice $V_{CCMIN}$, the voltage deemed to be the minimum necessary for continuous operation of control circuit 12. If battery 16 is fresh (e.g., near its beginning-of-life or BOL), a large drop in $V_{BATT}$ during the charging period is acceptable, as $V_{BATT}$ never drops below $V_{CCMIN}$. However, as battery 16 ages and its depletion level increases, $V_{BATT}$ may be drawn near or below $V_{CCMIN}$, which would interfere with proper functioning of the control circuitry.

As disclosed in the cited Pless et al patent, in the context of a cardiac pacemaker, one solution to this problem would be to place a small capacitor across the battery monitor $V_{BATT}$ during charging periods, and to interrupt the charging period each time $V_{BATT}$ falls below some predetermined voltage (e.g., a voltage some safety margin above the minimum $V_{CCMIN}$), and to restart the charging period after the battery voltage is restored. In the context of a cardiac pacemaker, the charge time is very short compared to a single timing cycle of the pulse generator (usually 0.3–1.0 second), and the prolongation of the charging cycle due to repeated interruptions is not extremely problematic in this context. In the context of an implantable defibrillator, however, a corresponding prolongation of the charging cycle would be much more problematic. For example, for a 20 second charging cycle, a 50% prolongation would be 10 seconds, and in the context of tachycardia or fibrillation, this could easily correspond to 30–40 heart cycles, during which time the arrhythmia may progress significantly.

Figure 3:
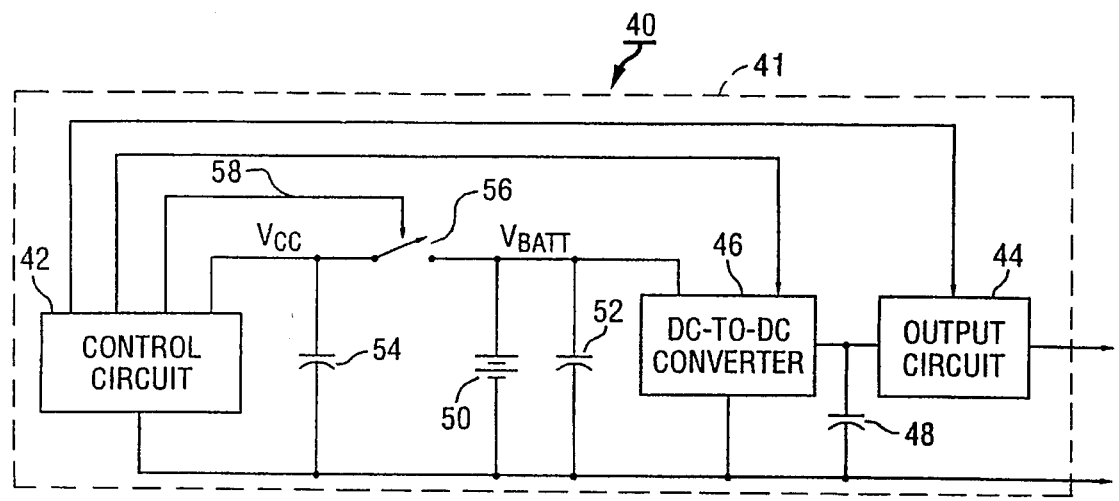
FIG. 3 is a block diagram of a battery-powered implantable medical device in accordance with one embodiment of the invention.

Turning now to FIG. 3, there is shown a schematic/block diagram of an implantable pulse generator 40 in accordance with one embodiment of the invention. Like device 10 from FIG. 1, device 40 in FIG. 3 includes a control circuit 42, an output circuit 44, and a DC-to-DC converter 46 for charging an output capacitor 48. DC-to-DC converter 46 draws the energy necessary for charging capacitor 48 from a battery 50. Also included in device 40 is a capacitance 52 which, like capacitance 22 in device 10, functions to minimize noise in the power supply to the various components of device 40 and to provide a low-impedance source for DC-to-DC converter 46. Note from FIG. 3 that battery 50 is shown as a single-cell battery, reflecting what is believed to be desirable in the field of automatic, body-implantable medical devices, as size is reduced.

In one embodiment, device 40 is an implantable cardioverter-defibrillator adapted to deliver cardioverting or defibrillating pulses to a patient's heart, on demand, via one or more elongate leads (not shown) in accordance with conventional practice. It is to be understood, however, that the present invention may be advantageously practiced in connection with various other types of battery-powered devices.

In accordance with conventional implantable device design, the device is enclosed in a hermetic enclosure illustrated schematically by broken line 41. Control circuit 42 in device 40 is coupled to DC-to-DC converter 46 and to output circuit 44, such that control circuit 42 can issue control signals to cause charging of output capacitor 48 and subsequently to cause discharge of output capacitor 48 through output circuit 44.

In accordance with an important aspect of the present invention, device 40 further includes a switch 56 interposed between control circuit 42 and battery 50, as well as a high energy density capacitor 54 coupled between the positive ($V_{CC}$) and negative (ground) power supply terminals of control circuit 42. An output signal line 58 from control circuit 42 enables control circuit 42 to selectively open and close switch 56. When switch 56 is closed, the battery output voltage $V_{BATT}$ is applied to the $V_{CC}$ input terminal of control circuit 42, and is also coupled to capacitor 54. Thus, capacitor 54 is charged by battery 50 when switch 56 is closed. When switch 56 is open, on the other hand, the operating voltage $V_{CC}$ for control circuit 42 is supplied from capacitor 54 alone; i.e., control circuit 42 is decoupled from battery 50.

In a presently preferred embodiment of the invention, and in accordance with a notable aspect of the invention, capacitor 54 is of a type known to have a very high energy density as compared to conventional tantalum or ceramic capacitors. Suitable capacitors for the purposes of the present invention include the double-layer or electrochemical types, electrostatic double-layer types, and so-called "pseudo-capacitor" technologies—"supercapacitors," "ultracapacitors," "dynacaps," "gold capacitors," and the like. See, e.g., Derman, "Electrochemical Caps Diversify," Electronic Engineering Times, pp. 58–61 (Jun. 20, 1994); Bullard, et al., "Operating Principles of the Ultracapacitor," IEEE Transactions on Magnetics, vol. 25, no. 1, pp. 102–106 (January 1989); Conway, "Transition from 'Supercapacitor' to 'Battery' Behavior in Electrochemical Energy Storage," Proceedings of the 34th International Power Sources Symposium, IEEE, New York, pp. 319–327 (1990); Morimoto, et al., "Characteristics of New Electric Double Layer Capacitor," Proceedings of the 33rd International Power Sources Symposium, The Electrochemical Society, Inc., pp. 618–623 (1988); Sikido, et al., "Electric Double Layer Capacitor, 'Gold Capacitor,'". New Materials and Processes, Matsushita Electric Industrial Co., Ltd., p. 184 (1981), all of which articles are incorporated herein by reference in their entireties.

Unlike conventional tantalum or ceramic capacitors, state-of-the-art high-density capacitor technology, as described in the foregoing references, is such that a capacitor can have a volume small enough to be practically incorporated into the hermetic enclosure of an implantable device (e.g., 1 cc or less) and also have a storage capacity (e.g. up to 10 millifarads) sufficient to provide, under most circumstances, continuous operating power ($V_{CC}$) to the device's control circuitry for the duration of an output capacitor charging cycle. For implantable devices generally, a capacitance in excess of 200 microfarads and a capacitance to volume ratio of 1 millifarad per cc is desired as a minimum. In the context of an implantable cardioverter or defibrillator, capacitor 54 preferably has a capacitance of 1-millifarad or greater and preferably a volume of less than 1 cubic centimeter. Such a capacitor is small enough to be practically incorporated into a body-implantable device, but has a capacity which enables it to provide operational power to control circuitry 42 for up to 20 seconds or more, depending upon the current required by the control circuitry 42, enabling it to operate such that the charging of the high voltage output capacitor would either not be interrupted, or interrupted only once during a typical defibrillation pulse charging cycle.

Figure 4:
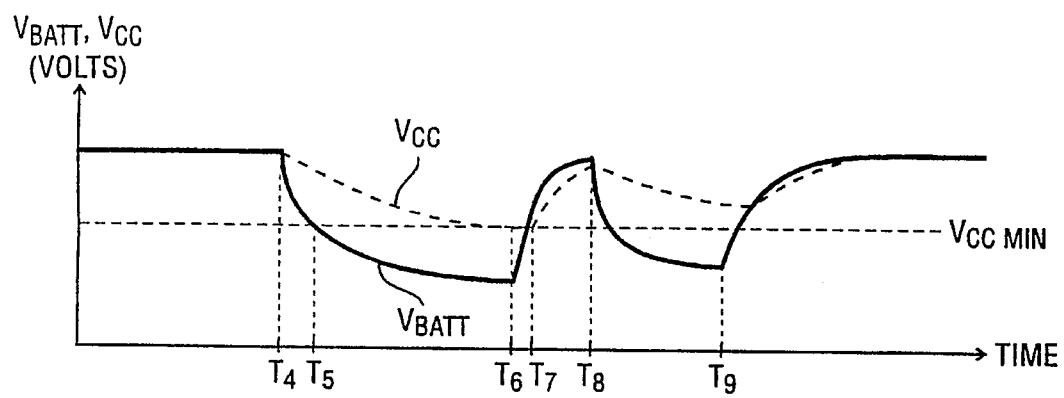
FIG. 4 is a plot of the battery output voltage and control circuit power supply voltage versus time for the device of FIG. 3.

Operation of device 40 in accordance with the presently disclosed embodiment of the invention will perhaps be best appreciated with reference to FIG. 4, which is a plot of $V_{CC}$ and $V_{BATT}$ versus time during a charging period for device 40. In FIG. 4, the charging period for device 40 begins at time T4, at which point the drain on battery 50 causes a steep drop in the battery's output voltage $V_{BATT}$. Prior to time T4, control circuitry 42 maintains switch 56 in a closed position, such that capacitor 54 is charged to $V_{BATT}$. When the charging period begins at time T4, control circuitry 42 asserts the signal on line 58 to cause switch 56 to open, so that operating voltage $V_{CC}$ for circuitry 42 is supplied from capacitor 54. (Those or ordinary skill in the art will appreciate that switch 56 may be implemented in various ways, such as with a simple field-effect transistor.) The high energy density of capacitor 54 is such that it can maintain $V_{CC}$ voltage supplied to control circuitry 42 at a level above $V_{CCMIN}$ for a to entire duration or a substantial portion of the charging period. Thus, even though the battery output voltage $V_{BATT}$ falls below $V_{CCMIN}$ at time T5 in FIG. 4 and remains there for a period of several seconds, $V_{CC}$ is maintained at an acceptable level.

If $V_{CC}$ reaches or nears $V_{CCMIN}$, as shown at time T6 in FIG. 4, control circuitry 42, will cause DC-to-DC converter 46 to temporarily halt the charging period, giving the battery 50 time to recover. When $V_{BATT}$ exceeds $V_{CC}$, control circuitry 42 will cause switch 56 to close, thereby allowing capacitor 54 to recharge (e.g., for a few hundred milliseconds or so). This occurs between times T7 and T8 in FIG. 4. Once battery 50 is given time to recover and capacitor 54 is charged, switch 56 is opened so that again $V_{CC}$ is supplied to control circuitry 42 from capacitor 54 alone, and the charging period is resumed. Once again, following time T8, $V_{BATT}$ falls below $V_{CCMIN}$, yet $V_{CC}$ from capacitor 54 is still at an acceptable level. It is to be noted that although FIG. 4 depicts a situation in which $V_{CC}$ from capacitor 54 reaches or nears $V_{CCMIN}$ during a charging period, this is generally not the case. In most instances, especially when battery 50 is nearer to beginning-of-life than end-of-life, the high energy density of capacitor 54 may be such that no interruption of the charging period is required, even if the battery voltage drops below the minimum level required to power the circuitry during the charging cycle. At time T9 in FIG. 4, the charging period is completed. At this time, switch 56 is closed, recharging capacitor 54 to $V_{BATT}$.

Operation of device 40 as just described is believed to be advantageous as compared with the prior art, since although the charging period may be temporarily interrupted, the high energy density of capacitor 54 is such that such interruptions are infrequent and short, ensuring acceptably short charging periods and an acceptable range of uncertainty as to the length of charging periods. Further, because the charging circuitry can continue operating for a substantial period of time while the battery voltage has fallen below the minimum necessary voltage level to power the control circuitry, a single cell battery may be practically employed, rather than a multiple cell battery as in present implantable cardioverters and defibrillators.

In one embodiment of the invention, it is contemplated that battery 50, switch 56, and capacitor 54 could be implemented as a unitary component, referred to herein as a "hybrid battery." Such a hybrid battery would have a negative output terminal to be coupled to both control circuit 42 and to DC-to-DC converter 46, a positive $V_{BATT}$ output terminal to be coupled to DC-to-DC converter 46, a separate positive $V_{CC}$ output terminal to be coupled to control circuit 42, and a control signal input terminal to receive the control signal from control circuit 42 to open and close switch 56.

Regarding generation of the signal on line 58 for controlling the opening and closing of switch 56, it is believed that this can be accomplished in a number of ways. In one embodiment, a simple voltage comparator circuit (not shown in the Figures) is coupled to the control input of switch 56, to capacitor 54, and to battery 52. The voltage comparator functions to keep switch 56 closed during non-peak operation of device 40 (i.e., whenever no charging period is occurring), and to keep switch 56 open during peak demand periods (i.e., during charging periods) so long as $V_{CC}$ (the output of capacitor 54) is greater than $V_{BATT}$. If $V_{CC}$ falls below $V_{BATT}$ or below the predetermined minimum acceptable level $V_{CCMIN}$, the comparator circuit would close switch 56. The comparator circuit may also be coupled to DC-to-DC converter 46 to momentarily interrupt charging periods as necessary, as described above. It is believed that it would be a matter of routine engineering for those of ordinary skill in the art to implement such a comparator circuit.

The foregoing description has not made reference to certain components of device 40 which are not believed to be relevant for the purposes of comprehending the present invention. It is believed, however, that those of ordinary skill in the art will readily appreciate how the present invention may be practiced in connection with particular classes of devices. For example, if device 40 is an implantable cardioverter-defibrillator, those of ordinary skill in the art will understand that device 40 will typically include sensing circuitry for monitoring one or more physiologic indicators of cardiac function (e.g., cardiac electrical signals, pressure signals, and the like), and will further include, as part of control circuit 42, circuitry for issuing signals for initiating certain events (charging cycles, stimulating pulse delivery cycles, and the like) in accordance with a predetermined operational mode of device 40. Thus, for example, if the sensing circuitry determines, based upon its monitoring of physiologic indicia of cardiac function, that the patient is undergoing an episode of tachycardia, control circuitry will issue the signals necessary to initiate a charging period and subsequently to trigger output circuit 44 into delivery of a cardioversion pulse to the patient's heart.

From the foregoing detailed description of a specific embodiment of the invention, it should be apparent that a method and apparatus for supplying power to various components of a battery-powered device has been disclosed. Although a specific embodiment of the invention has been described herein in some detail, this has been done solely for the purposes of illustrating various aspects of the invention and is not intended to be limiting with respect to the scope of the invention. It is contemplated that various modifications, alterations, and/or substitutions, including but not limited to those specifically noted herein, may be made to the disclosed embodiment of the invention without departing from the spirit and scope of the invention as defined in the appended claims.

What is claimed is:

1. A cardioverter, comprising:

a battery;

a high voltage output circuit including a high voltage energy storage device, said output circuit being responsive to a triggering signal to apply voltage stored on said energy storage device to an output terminal of said cardioverter;

a charging circuit means, coupled to said high voltage output circuit and to said battery, responsive to a charging signal, for charging said high voltage energy storage device;

a control circuit, coupled to said charging circuit and to said output circuit, said control circuit comprising means for issuing said triggering signal and said charging signal;

a high energy density capacitor operatively coupled to deliver voltage stored thereon to power said control circuit and having a sufficient capacitance to allow continued operation of said control circuit for at least one second while said charging circuit means charges said energy storage device;

switch means for selectively coupling and uncoupling said high energy density capacitor and said control circuitry coupled thereto from said battery; and means responsive to operation of said charging circuit for causing said switch means to uncouple said high energy density capacitor and said control circuit from said battery.

2. A cardioverter in accordance with claim 1 wherein said high energy density capacitor comprises an electrochemical, double-layer capacitor.

3. A cardioverter in accordance with claim 1 wherein said high energy density capacitor has a capacitance greater than 1-millifarad and a volume of less than 1 cubic centimeter.

4. A cardioverter in accordance with claim 1 wherein said battery comprises a single cell battery.

5. A cardioverter according to claim 1 wherein said responsive means comprises means for coupling said high energy density capacitor to said battery and interrupting charging of said high voltage energy storage device in response to voltage on said high energy density capacitor falling below a first predetermined level.

6. A cardioverter according to claim 5 wherein said responsive means comprises means for uncoupling said high energy density capacitor from said battery and causing resumption of charging of said high voltage energy storage device in response to voltage on said high energy density capacitor exceeding second, higher predetermined level.

7. An implantable medical device, comprising:

a hermetic enclosure;

a battery and circuitry means for performing a medically beneficial operation, both located in said enclosure, said circuitry means in turn comprising:

a first, control circuit, requiring a first level of electrical power when in operation;

a second, operational circuit, powered by said battery and requiring a second, higher level of electrical power when in operation;

a high energy density capacitor operatively coupled to deliver voltage stored thereon to power said first, control circuit and having a sufficient capacitance to provide power for continued operation of said first, control circuit for at least one second while said second, operational circuit is active;

switch means for selectively coupling and uncoupling said high energy density capacitor and said first, control circuit coupled thereto from said battery; and means responsive to operation of said second, operational circuit for causing said switch means to uncouple said high energy density capacitor and said control circuit from said battery.

8. A device in accordance with claim 7 wherein said high energy density capacitor comprises an electrochemical, double-layer capacitor.

9. A device in accordance with claim 7 wherein said high energy density capacitor has a capacitance greater than 1-millifarad and a volume of less than 1 cubic centimeter.

10. A device in accordance with claim 7 wherein said battery comprises a single cell battery.

11. A device according to claim 7 wherein said responsive means comprises means for coupling said high energy density capacitor to said battery and interrupting operation of said second operational circuit in response to voltage on said high energy density capacitor falling below a first predetermined level.

12. A device according to claim 11 wherein said responsive means comprises means for uncoupling said high energy density capacitor from said battery and causing resumption of operation of said second operational circuit in response to voltage on said high energy density capacitor exceeding second, higher predetermined level.

* * * * *